(12) United States Patent
Hourai et al.

(10) Patent No.: US 6,518,053 B2
(45) Date of Patent: Feb. 11, 2003

(54) THERMOSTABLE ESTERASE AND ITS GENE

(75) Inventors: Shinji Hourai, Toyonaka (JP); Yasushi Matsuki, Ashiya (JP)

(73) Assignee: Sumitomo Chemical Co., Ltd., Osaka (JP)

( * ) Notice: Subject to any disclaimer, the term of this patent is extended or adjusted under 35 U.S.C. 154(b) by 0 days.

(21) Appl. No.: 09/924,439

(22) Filed: Aug. 9, 2001

(65) Prior Publication Data

US 2002/0127686 A1 Sep. 12, 2002

Related U.S. Application Data

(62) Division of application No. 09/342,143, filed on Jun. 29, 1999, now Pat. No. 6,372,470.

(30) Foreign Application Priority Data

Jun. 30, 1998 (JP) ............................................. 10-184591

(51) Int. Cl.$^7$ ............................ C12N 9/16; C12N 1/20; C12N 15/00; C07H 21/04
(52) U.S. Cl. ................. 435/196; 435/252.3; 435/320.1; 435/471; 536/23.2
(58) Field of Search ............................... 435/196, 252.3, 435/320.1, 471; 536/23.2

(56) References Cited

FOREIGN PATENT DOCUMENTS

| JP | 7-163364 | 6/1995 |
| JP | 7-213280 | 8/1995 |

OTHER PUBLICATIONS

Rollence et al., *CRC Critical Reviews in Biotechnology*, vol. 8, No. 3, 1988, pp. 217–224.
Landt, et al., *Gene*, vol. 96, 1990, pp. 125–128.

*Primary Examiner*—Tekchand Saidha
(74) *Attorney, Agent, or Firm*—Birch, Stewart, Kolasch & Birch, LLP

(57) ABSTRACT

The present invention relates to an isolated or modified esterase having the excellent thermostable property which can be utilized for ester hydrolysis reaction, ester synthesis reaction, ester interchange reaction and its gene. The esterase is characterized in that it has at least a partial amino acid sequence necessary for expressing the thermostable esterase activity among the amino acid sequence shown by SEQ ID NO: 2 and further has an amino acid substitution described herein.

4 Claims, 11 Drawing Sheets

| | |
|---|---|
| GAGCGCGGAG GACACAGACC CGTGGACGAA | N43S |
| GGCGTGCTGA ACGCCATGGC CCCGCAGTAC | T240A |
| CAGCTGGGCA TCGCCCCCGG CTGGCCCGGC | V288A |
| GGCGGAACGG TCACCGAGGT CGCCATCGAG GGCGC | V325I |
| CCGCCGACCG AGTGAATCTA AATCCGCTCC | A363term |
| GACCATGATT ACGAATTCTT TTTTAATA | RV-G |
| GACCACCCGG TGCTGAGCCT GACCCTGCAG | RC-C |
| GGCGGAACGG TCACCGAGGT CGCCGTCGAG | RV-D |
| CGACGGCCAG TGCCAAGCTT GCATGCCGC | MY-2 |
| GTCGATGAGG CGCTGGATGA AGTCGGGGTT | MY-3 |
| CTCGACGGCG ACCTCGGTGA CCGTTCCGCC | MY-6 |

SEQUENCE LISTING

<160> NUMBER OF SEQ ID NOS: 24

<210> SEQ ID NO 1
<211> LENGTH: 1110
<212> TYPE: DNA
<213> ORGANISM: Chromobacterium SC-YM-1 (FERM BP-6703)
<220> FEATURE:
<221> NAME/KEY: CDS
<222> LOCATION: (1)..(1110)

<400> SEQUENCE: 1

```
atg act ctg ttc gat ggt atc act tcg cga atc gta gat act gat cgt     48
Met Thr Leu Phe Asp Gly Ile Thr Ser Arg Ile Val Asp Thr Asp Arg
 1               5                  10                  15 ctg act gtt aac atc ctg gaa cgt gcg gcc gac gac ccg cag acc ccg     96
Leu Thr Val Asn Ile Leu Glu Arg Ala Ala Asp Asp Pro Gln Thr Pro
             20                  25                  30 ccc gac cgc acg gtc gtg ttc gtc cac ggg aat gtg tcc tcc gcg ctg    144
Pro Asp Arg Thr Val Val Phe Val His Gly Asn Val Ser Ser Ala Leu
         35                  40                  45 ttc tgg cag gag atc atg cag gac ctg ccg agc gac ctg cgc gcc atc    192
Phe Trp Gln Glu Ile Met Gln Asp Leu Pro Ser Asp Leu Arg Ala Ile
     50                  55                  60 gcg gtc gac ctg cgc ggc ttc ggc ggc tcg gag cac gcg ccg gtc gac    240
Ala Val Asp Leu Arg Gly Phe Gly Gly Ser Glu His Ala Pro Val Asp
 65                  70                  75                  80 gcc acc cgc ggc gtc cgc gac ttc agc gac gat ctg cac gcg acc ctc    288
Ala Thr Arg Gly Val Arg Asp Phe Ser Asp Asp Leu His Ala Thr Leu
                 85                  90                  95 gag gcg ctc gac atc ccg gtc gcg cat ctg gtc ggc tgg tcg atg ggc    336
Glu Ala Leu Asp Ile Pro Val Ala His Leu Val Gly Trp Ser Met Gly
            100                 105                 110 ggc ggc gtc gtc atg cag tat gcc ctc gac cac ccg gtg ctg agc ctg    384
Gly Gly Val Val Met Gln Tyr Ala Leu Asp His Pro Val Leu Ser Leu
        115                 120                 125 acc ctg cag tcg ccg gtg tcg ccc tac ggc ttc ggc ggc acc cgc cgt    432
Thr Leu Gln Ser Pro Val Ser Pro Tyr Gly Phe Gly Gly Thr Arg Arg
    130                 135                 140
```

```
gac ggc tca cgc ctc acc gac gac gat gcc ggc tgc ggt ggc ggc ggt      480
Asp Gly Ser Arg Leu Thr Asp Asp Asp Ala Gly Cys Gly Gly Gly Gly
145                 150                 155                 160 gcg aac ccc gac ttc atc cag cgc ctc atc gac cac gac acc tcc gac      528
Ala Asn Pro Asp Phe Ile Gln Arg Leu Ile Asp His Asp Thr Ser Asp
                165                 170                 175 gat gcg cag acc tcg ccc cgg agc gtc ttc cgc gcc ggc tac gtc gcc      576
Asp Ala Gln Thr Ser Pro Arg Ser Val Phe Arg Ala Gly Tyr Val Ala
            180                 185                 190 tcg gac tac acc acc gac cac gag gac gtg tgg gtc gaa tcg atg ctc      624
Ser Asp Tyr Thr Thr Asp His Glu Asp Val Trp Val Glu Ser Met Leu
        195                 200                 205 acc acg tcc acc gcc gac gga aac tac ccc ggc gat gcg gtg ccg agc      672
Thr Thr Ser Thr Ala Asp Gly Asn Tyr Pro Gly Asp Ala Val Pro Ser
    210                 215                 220 gac aac tgg ccg ggc ttc gcc gcc ggc cgc cac ggc gtg ctg aac acc      720
Asp Asn Trp Pro Gly Phe Ala Ala Gly Arg His Gly Val Leu Asn Thr
225                 230                 235                 240 atg gcc ccg cag tac ttc gat gtg tcg ggg att gtc gac ctg gcc gag      768
Met Ala Pro Gln Tyr Phe Asp Val Ser Gly Ile Val Asp Leu Ala Glu
                245                 250                 255 aag cct ccg atc ctg tgg atc cac ggc acc gcg gac gcg atc gtc tcc      816
Lys Pro Pro Ile Leu Trp Ile His Gly Thr Ala Asp Ala Ile Val Ser
            260                 265                 270 gac gcg tcg ttc tac gac ctc aac tac ctc ggc cag ctg ggc atc gtc      864
Asp Ala Ser Phe Tyr Asp Leu Asn Tyr Leu Gly Gln Leu Gly Ile Val
        275                 280                 285 ccc ggc tgg ccc ggc gaa gac gtc gcg ccc gcg cag gag atg gtg tcg      912
Pro Gly Trp Pro Gly Glu Asp Val Ala Pro Ala Gln Glu Met Val Ser
    290                 295                 300 cag acc cgc gat gtc ctc ggc cgc tac gct gcg ggc ggc gga acg gtc      960
Gln Thr Arg Asp Val Leu Gly Arg Tyr Ala Ala Gly Gly Gly Thr Val
305                 310                 315                 320 acc gag gtc gcc gtc gag ggc gcg ggc cac tcc gcg cac ctg gag cgt     1008
Thr Glu Val Ala Val Glu Gly Ala Gly His Ser Ala His Leu Glu Arg
                325                 330                 335 ccc gcg gtg ttc cgc cac gcg ctg ctc gag atc atc ggc tac gtc ggc     1056
Pro Ala Val Phe Arg His Ala Leu Leu Glu Ile Ile Gly Tyr Val Gly
            340                 345                 350 gcg gcg gcc gac ccc gcc ccg ccg acc gag gcg atc atc atc cgc tcc     1104
Ala Ala Ala Asp Pro Ala Pro Pro Thr Glu Ala Ile Ile Ile Arg Ser
        355                 360                 365 gcc gac                                                              1110
Ala Asp
    370

<210> SEQ ID NO 2
<211> LENGTH: 370
<212> TYPE: PRT
<213> ORGANISM: Chromobacterium SC-YM-1 (FERM BP-6703)

<400> SEQUENCE: 2

Met Thr Leu Phe Asp Gly Ile Thr Ser Arg Ile Val Asp Thr Asp Arg
 1               5                  10                  15

Leu Thr Val Asn Ile Leu Glu Arg Ala Ala Asp Asp Pro Gln Thr Pro
                20                  25                  30

Pro Asp Arg Thr Val Val Phe Val His Gly Asn Val Ser Ser Ala Leu
            35                  40                  45

Phe Trp Gln Glu Ile Met Gln Asp Leu Pro Ser Asp Leu Arg Ala Ile
        50                  55                  60
```

```
Ala Val Asp Leu Arg Gly Phe Gly Gly Ser Glu His Ala Pro Val Asp
 65                  70                  75                  80

Ala Thr Arg Gly Val Arg Asp Phe Ser Asp Asp Leu His Ala Thr Leu
                 85                  90                  95

Glu Ala Leu Asp Ile Pro Val Ala His Leu Val Gly Trp Ser Met Gly
            100                 105                 110

Gly Gly Val Met Gln Tyr Ala Leu Asp His Pro Val Leu Ser Leu
        115                 120                 125

Thr Leu Gln Ser Pro Val Ser Pro Tyr Gly Phe Gly Thr Arg Arg
    130                 135                 140

Asp Gly Ser Arg Leu Thr Asp Asp Ala Gly Cys Gly Gly Gly
145                 150                 155                 160

Ala Asn Pro Asp Phe Ile Gln Arg Leu Ile Asp His Asp Thr Ser Asp
                165                 170                 175

Asp Ala Gln Thr Ser Pro Arg Ser Val Phe Arg Ala Gly Tyr Val Ala
            180                 185                 190

Ser Asp Tyr Thr Thr Asp His Glu Asp Val Trp Val Glu Ser Met Leu
        195                 200                 205

Thr Thr Ser Thr Ala Asp Gly Asn Tyr Pro Gly Asp Ala Val Pro Ser
210                 215                 220

Asp Asn Trp Pro Gly Phe Ala Ala Gly Arg His Gly Val Leu Asn Thr
225                 230                 235                 240

Met Ala Pro Gln Tyr Phe Asp Val Ser Gly Ile Val Asp Leu Ala Glu
                245                 250                 255

Lys Pro Pro Ile Leu Trp Ile His Gly Thr Ala Asp Ala Ile Val Ser
            260                 265                 270

Asp Ala Ser Phe Tyr Asp Leu Asn Tyr Leu Gly Gln Leu Gly Ile Val
        275                 280                 285

Pro Gly Trp Pro Gly Glu Asp Val Ala Pro Ala Gln Glu Met Val Ser
290                 295                 300

Gln Thr Arg Asp Val Leu Gly Arg Tyr Ala Ala Gly Gly Thr Val
305                 310                 315                 320

Thr Glu Val Ala Val Glu Gly Ala Gly His Ser Ala His Leu Glu Arg
                325                 330                 335

Pro Ala Val Phe Arg His Ala Leu Leu Glu Ile Ile Gly Tyr Val Gly
            340                 345                 350

Ala Ala Ala Asp Pro Ala Pro Pro Thr Glu Ala Ile Ile Ile Arg Ser
        355                 360                 365

Ala Asp
370

<210> SEQ ID NO 3
<211> LENGTH: 44
<212> TYPE: DNA
<213> ORGANISM: Artificial Sequence
<220> FEATURE:
<221> NAME/KEY: modified_base
<222> LOCATION: (1)..(44)
<223> OTHER INFORMATION: any n = i (inosine)
<223> OTHER INFORMATION: Description of Artificial Sequence:
      Oligonucleotide

<400> SEQUENCE: 3
acnctnttcg acggnatcac ntgncgnatc gtngacacng accg                    44

<210> SEQ ID NO 4
```

```
<211> LENGTH: 44
<212> TYPE: DNA
<213> ORGANISM: Artificial Sequence
<220> FEATURE:
<221> NAME/KEY: modified_base
<222> LOCATION: (1)..(44)
<223> OTHER INFORMATION: any n = i (inosine)
<223> OTHER INFORMATION: Description of Artificial Sequence:
      Oligonucleotide

<400> SEQUENCE: 4
acnctnttcg acggnatcac ntcncgnatc gtngacacng accg            44

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide LP-1

<400> SEQUENCE: 5 aattctttt taataaaatc                                        20

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide LP-2

<400> SEQUENCE: 6
ttttcctcct gattttatta aaaaag                                26

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide ES-3

<400> SEQUENCE: 7
ggtatcactt cgcgaatcgt agatactgat                            30

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide ES-4

<400> SEQUENCE: 8
ggccgcacgt tccaggatgt taacagtcag acgatcagta tctac           45

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide ES-5

<400> SEQUENCE: 9
cgtctgactg ttaacatcct ggaacgtgc                             29
```

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence:
      Oligonucleotide ES-6

<400> SEQUENCE: 10
gattcgcgaa gtgataccat cgaacagagt catatgt                37

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide ES-7

<400> SEQUENCE: 11
aggaggaaaa aacatatgac tctgttcgat                30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide N43S

<400> SEQUENCE: 12
cagcgcggag gacacagacc cgtggacgaa                30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide T240A

<400> SEQUENCE: 13
ggcgtgctga acgccatggc cccgcagtac                30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide V288A

<400> SEQUENCE: 14
cagctgggca tcgcccccgg ctggcccggc                30

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence:
      Oligonucleotide V325I

<400> SEQUENCE: 15
ggcggaacgg tcaccgaggt cgccatcgag ggcgc                35

```
<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide A363term

<400> SEQUENCE: 16
ccgccgaccg agtgaatcta aatccgctcc                                    30

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide RV-G

<400> SEQUENCE: 17
gaccatgatt acgaattctt ttttaata                                      28

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide RC-C

<400> SEQUENCE: 18
gaccacccgg tgctgagcct gaccctgcag                                    30

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide RV-D

<400> SEQUENCE: 19
ggcggaacgg tcaccgaggt cgccgtcgag                                    30

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide MY-2

<400> SEQUENCE: 20
cgacggccag tgccaagctt gcatgccgc                                     29

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide MY-3

<400> SEQUENCE: 21
gtcgatgagg cgctggatga agtcggggtt                                    30
```

```
<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide MY-6

<400> SEQUENCE: 22
ctcgacggcg acctcggtga ccgttccgcc                                    30

<210> SEQ ID NO 23
<211> LENGTH: 109
<212> TYPE: DNA
<213> ORGANISM: Artificial Sequence
<220> FEATURE:
<223> OTHER INFORMATION: Description of Artificial Sequence:
      double stranded DNA fragment (SD)

<400> SEQUENCE: 23
aattcttttt taataaaatc aggaggaaaa aacatatgac tctgttcgat ggtatcactt    60
cgcgaatcgt agatactgat cgtctgactg ttaacatcct ggaacgtgc              109

<210> SEQ ID NO 24
<211> LENGTH: 109
<212> TYPE: DNA
<213> ORGANISM: Artificial Sequence
<220> FEATURE:
<223> OTHER INFORMATION: Description of Artificial Sequence:
      double stranded DNA fragment (SD)

<400> SEQUENCE: 24
gaaaaaatta ttttagtcct ccttttttgt atactgagac aagctaccat agtgaagcgc    60
ttagcatcta tgactagcag actgacaatt gtaggacctt gcacgccgg              109
```

THERMOSTABLE ESTERASE AND ITS GENE

This application is a divisional of U.S. Ser. No. 09/342,143, filed Jun. 29, 1999, now U.S. Pat. No. 6,372,470.

BACKGROUND OF THE INVENTION

1. Field of the Invention

The present invention relates to an esterase having the excellent thermostable property which can be utilized for ester hydrolysis reaction, ester synthesis reaction, ester interchange reaction and the like and its gene.

2. Description of the Related Art

Esterase is an enzyme which hydrolyzes an ester linkage and has ability to catalyze ester synthesis and ester interchange reaction, and has been recently utilized in organic synthesis reaction for manufacturing medicaments, pesticides or intermediates thereof.

It is desirable that the esterase, which is industrially utilized, has high stability to temperature, pH, solvent, pressure and the like. Inter alia, where the esterase has high thermostability, the reaction temperature can be elevated, enabling the reaction rate to be enhanced and an inactivation of the enzyme to be reduced. Accordingly, there is desired the esterase having the excellent thermostability for shortening the reaction time and promoting the reaction efficiency.

DISCLOSURE OF THE INVENTION

Under these circumstances, the present inventors studied hard using the technique of introducing mutation into gene by site-directed mutagenesis and, as a result, found that mutant esterase having the amino acid sequence where the particular amino acid in the wild-type amino acid sequence is substituted shows the excellent thermostability, which resulted in completion of the present invention.

That is, the present invention provides:

1. an esterase (hereinafter referred to as "the present esterase") which is characterized in that it has at least a partial amino acid sequence necessary for expressing the thermostable esterase activity among the amino acid sequence shown by SEQ ID NO:2 having any one of the following amino acid substitutions:
    (1) amino acid substitution where 325th amino acid in the amino acid sequence shown by SEQ ID NO:2 is substituted with isoleucine,
    (2) amino acid substitution where 240th amino acid in the amino acid sequence shown by SEQ ID No:2 is substituted with alanine and 288th amino acid is substituted with alanine,
    (3) amino acid substitution where 43rd amino acid in the amino acid sequence shown by SEQ ID No:2 is substituted with serine,
2. an esterase which is characterized in that it has at least a partial amino acid sequence necessary for expressing the thermostable esterase activity among the amino acid sequence shown by SEQ ID No:2 having amino acid substitution where 325th amino acid in the amino acid sequence shown by SEQ ID No:2 is substituted with isoleucine,
3. an esterase which is characterized in that it has at least a partial amino acid sequence necessary for expressing the thermostable esterase activity among the amino acid sequence shown by SEQ ID No:2 having amino acid substitution where 240th amino acid in the amino acid sequence shown by SEQ ID No:2 is substituted with alanine, and 288th amino acid is substituted with alanine,
4. an esterase which is characterized in that it has at least a partial amino acid sequence necessary for expressing the thermostable esterase activity among the amino acid sequence shown by SEQ ID NO:2 having amino acid substitution where 43rd amino acid in the amino acid sequence shown by SEQ ID No:2 is substituted with serine,
5. a gene which is characterized in that it encodes the esterase of the above 1 to 4,
6. a plasmid which is characterized in that it contains the gene of the above 5,
7. a microorganism which is characterized in that it contains the plasmid of the above 6,
8. a process for producing an esterase which is characterized by comprising culturing the microorganism of the above 4 and, thereby, allowing the microorganism to produce an esterase having at least a partial amino acid sequence necessary for expressing the thermostable esterase activity among the amino acid sequence shown by SEQ ID No:2 having any one of the following amino acid substitutions:
    (1) amino acid substitution where 325th amino acid in the amino acid sequence shown by SEQ ID No:2 is substituted with isoleucine,
    (2) amino acid substitution where 240th amino acid in the amino acid sequence shown by SEQ ID No:2 is substituted with alanine and 288th amino acid is substituted with alanine,
    (3) amino acid substitution where 43rd amino acid in the amino acid sequence shown by SEQ ID No:2 is substituted with serine.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

BRIEF DESCRIPTION OF THE DRAWINGS

FIG. 4 is a view showing a base sequence of a synthetic oligonucleotide used for introducing a site-directed mutation into 43rd amino acid, 240th amino acid, 288th amino acid, 325th amino acid and 363rd amino acid of the wild-type esterase (SEQ ID NOS:12–22 are shown from top to bottom in FIG. 4).

DETAILED DESCRIPTION OF THE INVENTION

Figure 1:
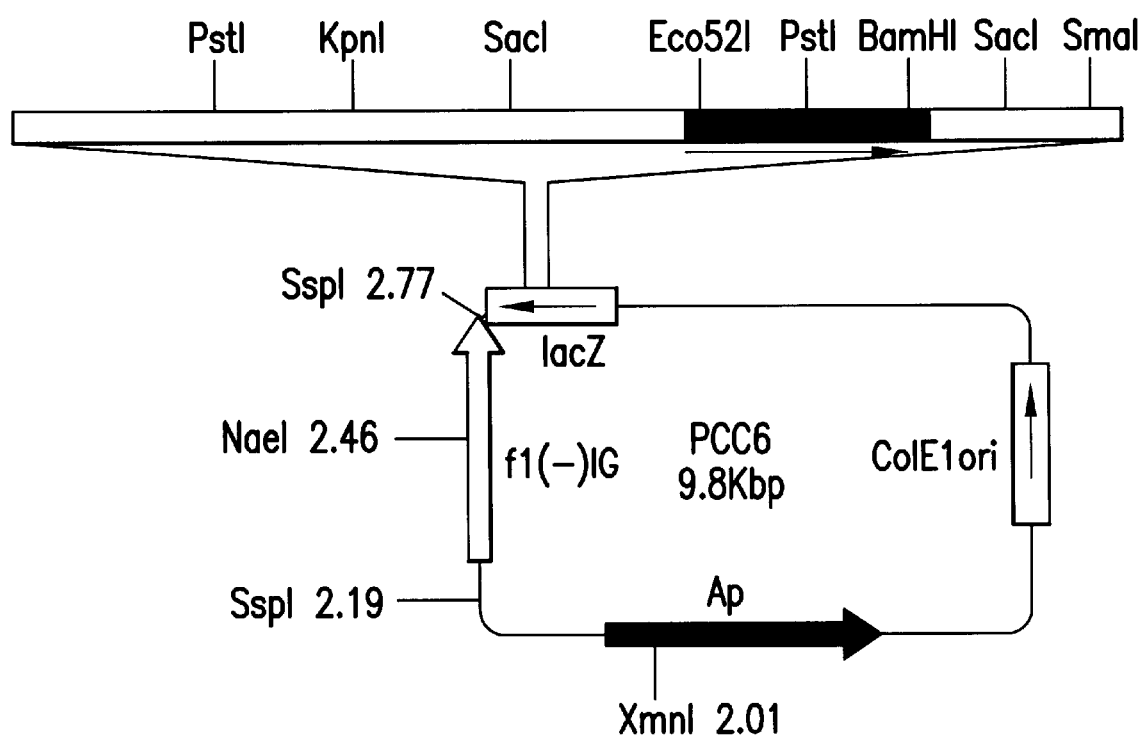
FIG. 1 is a view showing a restriction enzyme map of a plasmid pCC6 containing a gene encoding a wild-type esterase.

The present invention will be described in detail below.

Esterase having the amino acid sequence shown by SEQ ID No:2 (hereinafter referred to as "wild-type esterase") is an esterase described in JP-A-7-163364. (1995). The esterase activity of the esterase or the present esterase can be determined by mixing with, for example, p-nitrophenyl acetate (pNPA), holding a temperature at 37° C. and quantitating the amount of released p-nitrophenyl using absorbance of the reaction solution at 410 nm. In the present esterase, "the thermostable esterase activity" means that the remaining activity percentage is, for instance, high as compared with the wild-type esterase even after holding a temperature at 70° C. for 120 minutes.

In addition, in the present esterase, "at least, a partial amino acid sequence necessary for expressing the thermostable esterase activity" is, for example, an esterase comprising 362 amino acids corresponding to at lease 1st to 362nd amino acids in the amino acid sequence shown by SEQ ID No:2, and its equivalents which have the same biological function.

In order to obtain a gene (hereinafter referred to as "the present gene") which is characterized in that it encodes the present esterase, a gene encoding the wild-type esterase (hereinafter referred to as "wild-type gene") may be firstly obtained. The wild-type gene is, for example, a gene having the base sequence shown by SEQ ID No:1 and may be obtained from microorganisms belonging to genus Chromobacterium retained by a microorganism retaining organization and the like according to the conventional genetic engineering technique described in, for example, J. Sambrook, E. F. Fritsch, T. Maniatis; Molecular Cloning 2nd edition, published by Cold Spring Harbor Laboratory, 1989. That is, a microorganism belonging to genus Chromobacterium is cultured using, for example, LB medium (tryptophane 1.0%, yeast extract 0.5%, NaCl 0.5%), the cells of the microorganism obtained by culturing are disrupted according to the conventional method such as ultrasonic disruption and the like, treated with protease, and genomic DNA is extracted. The resulting genomic DNA is cleaved with a suitable restriction enzyme, and inserted into λ gtII which is a phage vector or pUC19 which is a plasmid vector and the like using a ligase to make a genomic DNA library. This can be screened with, for example, a screening method such as hybridization method using a synthetic DNA probe corresponding to the portion of the amino acid sequence of the wild-type esterase, a method for measuring the activity of the wild-type esterase and the like, to obtain a clone containing the wild-type gene. As a synthetic DNA probe corresponding to the portion of the amino acid sequence of the wild-type esterase, in particularly, for example, an oligonucleotide having the base sequence shown by SEQ ID No:3 and an oligonucleotide having the base sequence shown by SEQ ID No:4 may be used.

The present gene may be prepared by introducing a site-directed mutation into the wild-type gene. As a site-directed mutation introducing method, there are, for example, a method by Olfert Landt et al. (Gene, 96, 125–128, 1990), a method by Smith et al. (Genetic Engineering, 31, Setlow, J. and Hollaender, A. Plenum:New York), a method by Vlasuk et al. (Experimental Manipulation of Gene Expression, Inouye, M.: Academic Press, New York), a method by Hos.N.Hunt et al. (Gene, 77, 51, 1989) and the like.

For example, in order to prepare the present gene where 325th amino acid in the amino acid sequence shown by SEQ ID No:2 is substituted with isoleucine, a plasmid DNA which contains the wild-type gene having a base sequence shown by SEQ ID No:1 is first prepared according to the method described in, for example, J. Sambrook, E. F. Fritsch, T. Maniatis; Molecular Cloning 2nd edition, published by Cold Spring Harbor Laboratory, 1989 and the like. Then, by using the plasmid DNA as a template, and by using as one side primer an oligonucleotide comprising a base sequence corresponding to the amino acid sequence where 325th amino acid in the amino acid sequence shown by SEQ ID No:2 is substituted with isoleucine (for example, oligonucleotide having a base sequence shown by SEQ ID No:15) and as the other side primer an oligonucleotide having a base sequence shown by SEQ ID No:20, amplification may be performed by a PCR method. Here, PCR reaction conditions are as follows: after maintaing a temperature at 94° C. for 5 minutes, 20 cycles of treatment of maintaining a temperature at 94° C. for 1 minute, then at 50° C. for 2 minutes and at 75° C. for 3 minutes are carried out and finally a temperature is maintained at 75° C. for 8 minutes. The DNA fragment thus amplified may be digested with, for example, restriction enzyme BstPI and XbaI, and ligation-reacted with the plasmid DNA comprising the wild-type esterase gene same digested with the same restriction enzyme to obtain the desired present gene.

In addition, an oligonucleotide comprising a base sequence corresponding to the amino acid sequence where 240th amino acid in the amino acid sequence shown by SEQ ID No:2 is substituted with alanine and 288th amino acid is substituted with alanine and an oligonucleotide comprising a base sequence corresponding to the amino acid sequence where 43rd amino acid in the amino acid sequence shown by SEQ ID No:2 is substituted with serine may be prepared using a similar method to that described above. The detail thereof is described as Examples.

By using the present gene thus prepared, the present esterase may be produced and obtained at a large amount according to the conventional genetic engineering method. More particularly, for example, a plasmid which can express the present gene in the host microorganism is prepared, which may be introduced into the host microorganism to transform to make a transformant microorganism. Then, the resultant transformant microorganism may be cultured according to the conventional microorganism culturing method.

The example of the above plasmid are those that can be replicated in the host microorganism and is easily isolated and purified from the host microorganism. Preferably, mention may be made of a plasmid where the present gene is introduced into an expression vector having a promoter and a detectable marker. As an expression vector, various commercially available vectors may be used. For example, in the case of expression in *E. coli,* an expression vector comprising a promoter such as lac, trp, tac and the like (manufactured by Pharmacia Biotech and the like) may be used.

As a host microorganism, both eukaryote and prokaryote can be used and an example thereof is *E. coli* and the like. The above plasmid may be introduced into the host microorganism by the conventional genetic engineering method to transform the host microorganism.

Culturing of the microorganism (hereinafter referred to as the present microorganism) harboring the plasmid containing the present gene thus obtained may be performed according to the conventional microorganism culturing method. For example, where the host microorganism is *E. coli,* culturing is performed in a medium appropriately containing a suitable carbon source, a nitrogen source and a minor nutrient such as vitamines. As a culturing method, both solid culturing and liquid culturing are possible and, preferably, mention may be made of an aerated stirring culturing method.

The present microorganism producing the present esterase thus prepared may be utilized for producing a useful compound such as medicaments, pesticides, and intermediates thereof and the like as a bioreactor for ester hydrolyzation, ester synthesization, ester interchage reaction or the like.

In addition, from the cells obtained by culturing the present microorganism, an extract containing the present esterase may be prepared or the present esterase may be collected and purified and these may be utilized as an enzyme reactor. Collection and purification of esterase from the cells obtained by culturing the present microorganism may be performed by suitably combining the conventional protein extracting, isolating and purifying methods. For example, after completion of the culturing, the cells of the present microorganism are collected by centrifugation or the like, disrupted or lyzed and the present esterase may be collected and purified by combining the steps using various chromatographies such as ion exchange, hydrophobicity, gel filtration and the like.

The present microorganism and the present esterase described above may be utilized as a reactor by immobilizing onto a suitable carrier.

EXAMPLE

The following Examples illustrate the present invention in detail but the present invention is not limited to them.

Example 1

Preparation of Wild-type Gene: Preparation of Genomic DNA

Chromobacterium strain SC-YM-1 (this strain was originally deposited in National Institute of Bioscience and Human-Technology Agency of Industrial Science and Techonology as an ascession No. FERM P-14009 by the applicant on Dec. 9, 1993 and at present continuously deposited as an accession No. FERMBP-6703 under Budapest Treaty) was cultured by shaking in 5 ml of a medium for pre-culturing (glucose 1% (w/v), yeast extract 1% (w/v), $K_2HPO_4$ 0.1% (w/v), $MgSO_4$ 0.02% (w/v), pH7.3) at 30° C. for 24 hours and the resulting culture solution was inoculated on 1000 ml of medium for culturing (glucose 1% (w/v), yeast extract 1% (w/v), $K_2KPO_4$ 0.1% (w/v), $MgSO_4$ 0.02% (w/v), pH 7.3), followed by culturing at 30° C. Upon this, when $OD_{660}$ reached 3.4, penicillin G was added to the final concentration of 2 units/ml culture solution and culturing was continued until $OD_{660}$ reached 10.

The cells were collected by centrifugation (8000×g, 10 min., 4° C.), the cells were suspended in 80 ml of 10 mM Tris buffer (pH 8.0), 25% (w/v) sucrose solution, and to this was Lysozyme egg white (manufactured by Seikagaku corporation) to the final concentration of 5 mg/ml, followed by incubation at 37° C. for 30 minutes. Then, 10 ml of 10% (w/v) SDS was added and protease K (manufactured by Boehringer) was added to the final concentration of 200 µg/ml, followed by incubation at 37° C. for 3 hours. Thereafter, extraction was performed with an equivalent volume of 0.1M Tris-saturated phenol three times and with ether two times, and 2 volumes of ethanol was added to the aqueous layer to stir, followed by centrifugation (12000×g, 30 min., 4° C.). The resulting precipitates were dried and dissolved in 20 ml of Tris EDTA buffer (10 mM Tris-HCl, 1mM EDTA, pH 8.0), and subjected to CsCl-EtBr equilibrium density-gradient ultracentrifugation (275000×g, 18 hours, 25° C.) to recover the band-likely converged DNA which was dialyzed against Tris EDTA buffer (10 mM Tris-HCl, 1 mM EDTA, pH 8.0) to obtain about 5.4 mg of genomic DNA.

Example 2

Preparation of Wild-type Gene: Preparation of Genomic DNA Library

100 µg of the genomic DNA obtained in Example 1 was digested with XhoI (manufactured by Takara Shuzo Co., Ltd.). On the other hand, 1 µg of λ phage λ ZAPII (manufactured by Stratagene) was digested with XhoI, mixed with the genomic DNA digests, and a ligase (manufactured by Takara Shuzo Co., Ltd.) was added to maintain at 16° C. overnight.

Then, the DNA contained in this reaction solution was packed into λ phage A ZAPII using an in vitro packaging kit (manufactured by Stratagene) and *E. coli* strain XL-1blue to make the genomic DNA library.

Example 3

Preparation of Wild-type Gene: Screening of Genomic DNA Library

1. Preparation of Synthetic DNA Probe and Labeling with Isotope 44-mer oligonucleotides having a base sequences shown by SEQ ID Nos:3–4 were synthesized based on the amino acid sequence of the N-terminal of the wild-type esterase. The synthesis of the oligonucleotides was performed using a DNA synthesizer (Applied Biosystems Model 394A).

Into 50 pmol of this oligonucleotide were mixed 3 µl of 0.5M Tris-HCl (pH 7.6), 0.1M $MgCl_2$, 0.05M DTT, 0.001M EDTA, 10 units of T4 Polynucleotide Kines (manufactured by Takara Shuzo Co., Ltd.) and 10 µl of [γ $^{32}$P]ATP (manufactured by Amersham), which was maintained at 37° C. for 60 minutes, and subjected to gel filtration by Sephadex G-50 (manufactured by Pharmacia) to make a DNA probe labeled with an isotope.

2. Screening of Genomic DNA Library

*E. coli* infected with the phage of the genomic DNA library made in Example 2 was spread on a plate to culture, a nitrocellulose filter was tightly contacted on the surface of the plate and mildly peeled. The filter was soaked into 1.5 M NaCl-0.5 M NaOH solution, and then soaked into 1.5 M NaCl-0.5 M Tris-HCl (pH 8.0) solution to neutralize. Thereafter, the filter was washed with 0.36 M NaCl-20 mM $NaH_2PO_4$ (pH 7.5)-2 mM EDTA (pH 7.5) and then dried.

Then, by using the filter and the isotope-labeled DNA probe corresponding to the N-terminal amino acid sequence of the wild-type esterase prepared above, plaque hybridization was performed by the following method. That is, the filter was maintained at 60° C. for 30 minutes in a solution containing 4×SSC, 1% (w/v) SDS, 10×Dendhart (0.2% (w/v) Ficoll, 0.2% (w/v) polyvinyl pyrrolidone and 0.2% (w/v) bovine serum albumin), and maintained at 60° C. for 5 hours in a solution containing 5×SSC, 5×Dendhart and 100 μg/ml salmon sperm DNA. Hybridization was performed by placing a solution containing 5×SSC, 5×Dendhart and 100 μg/ml salmon sperm DNA and the filter in a plastic bag, adding the isotope-labeled DNA probe at about 5×105 cpm per filter and maintaining at 60° C. overnight.

The filter by which hybridization was performed as above was washed by successively maintaining 1) at 60° C. for 15 minutes in a solution containing 2×SSC and 0.5% (w/v) SDS, 2) at 25° C. for 30 minutes in a solution containing 2×SSC and 0.5% (w/v) SDS, 3) at 60° C. for 15 minutes in a solution containing 2×SSC and 0.5% SDS(w/v), air-dried and autoradiographed by contacting with a X-ray film (FUJI RX) and an intensifying paper at −80° C. overnight. As a result, a plaque giving a positive signal was obtained. The desired plaque, helper phage and *E. coli* were mixed, cultured at 37° C. for 4 hours and maintained at 70° C. for 20 minutes according to the conventional method described by authors, J. Sambrook, E. F. Fritsch, T. Maniatis; Molecular Cloning 2nd edition, published by Cold Spring Harbor Laboratory, 1989. *E. coli* was infected with the supernatant and cultured to obtain a transformant growing in a medium containing ampicillin. A plasmid DNA was prepared from the resultant transformant, the base sequence thereof was determined by a dideoxy method and, as a result, it was found that the resultant clone did not encode the full length of an esterase gene. Then, by using a DNA fragment having a portion of the sequence as a probe, screening by plaque hybridization was performed again. Upon this, a libraty was used which was made by partially digesting the genomic DNA with Sau3AI (manufactured by Takara Shuzo Co., Ltd.) and ligating to λ phage λ ZAPII (manufactured by Stratagene). As a result, a plaque giving a positive signal was obtained. A plasmid DNA was prepared from the plaque according to the same method as that described above, the base sequence was determined and, as a result, it was found that it encoded the full length of an esterase gene. Thus, the plasmid pCC6 (FIG. 1) was obtained.

Example 4

Expression Plasmid Containing Wild-type Gene

In order to convert the base sequence around an initiation codon of the wild-type gene and that 5' upstream thereof into a sequence suitable for gene expression in *E. coli*, oligonucleotides having a base sequences shown by SEQ ID Nos:5–11 were synthesized using a DNA synthesizer Model 394A (manufactured by Applied Biosystems).

LP-1 (SEQ ID No:5)
LP-2 (SEQ ID No:6)
ES-3 (SEQ ID No:7)
ES-4 (SEQ ID No:8)
ES-5 (SEQ ID No:9)
ES-6 (SEQ ID No:10)
ES-7 (SEQ ID No:11)

The 5' terminals of oligonucleotides LP-2, ES-3, ES-5, ES-6 and ES-7 were phosphorylated, ligated with LP-1 and ES-5, and annealed to prepare a double-stranded DNA fragment (SD) comprising the following base sequence (SEQ ID NOS:23 and 24) . The double-stranded DNA fragment (SD) was phosphorylated at its both ends.

```
(SD)

<       LP-1        >  <          ES-7        >  <
        AATTCTTTTT TAATAAAATC AGGAGGAAAA AACATATGAC TCTGTTCGAT GGTATCACTT

GAAAAA ATTATTTTAG TCCTCCTTTT TTGTATACTG AGACAAGCTA CCATAGTGAA
                <           LP-2           >  <              ES-6
        EcoRI

ES-3       > <          ES-5            >
        CGCGAATCGT AGATACTGAT CGTCTGACTG TTAACATCCT GGAACGTGC

GCGCTTAGCA TCTATGACTA GCAGACTGAC AATTGTAGGA CCTTGCACGC CGG
                 > <                        ES-4                  >
                                                         Eco52I
```

Figure 2:
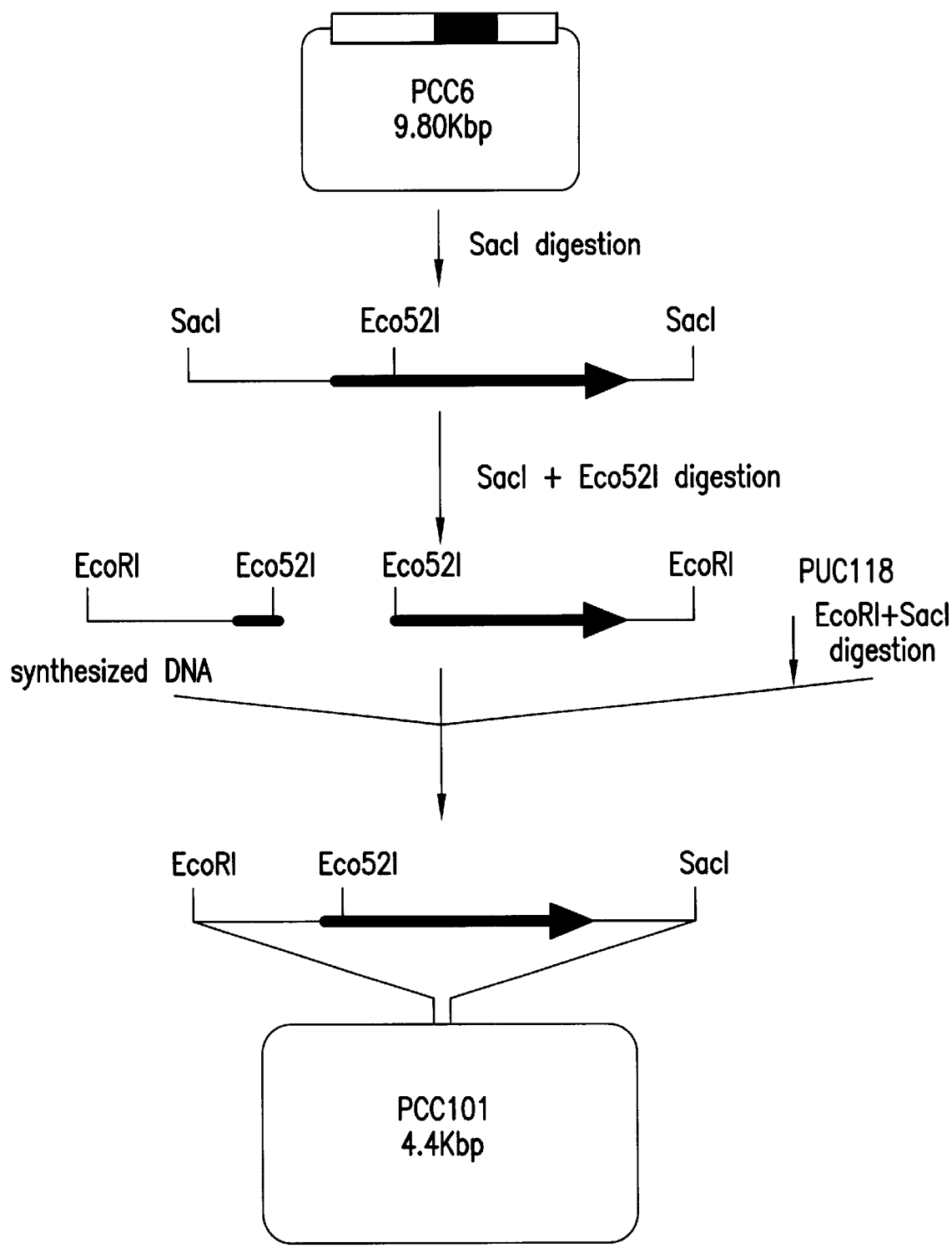
FIG. 2 is a view showing a step of constructing the expression plasmid pCC101 containing a gene encoding the wild-type esterase.
Figure 3:
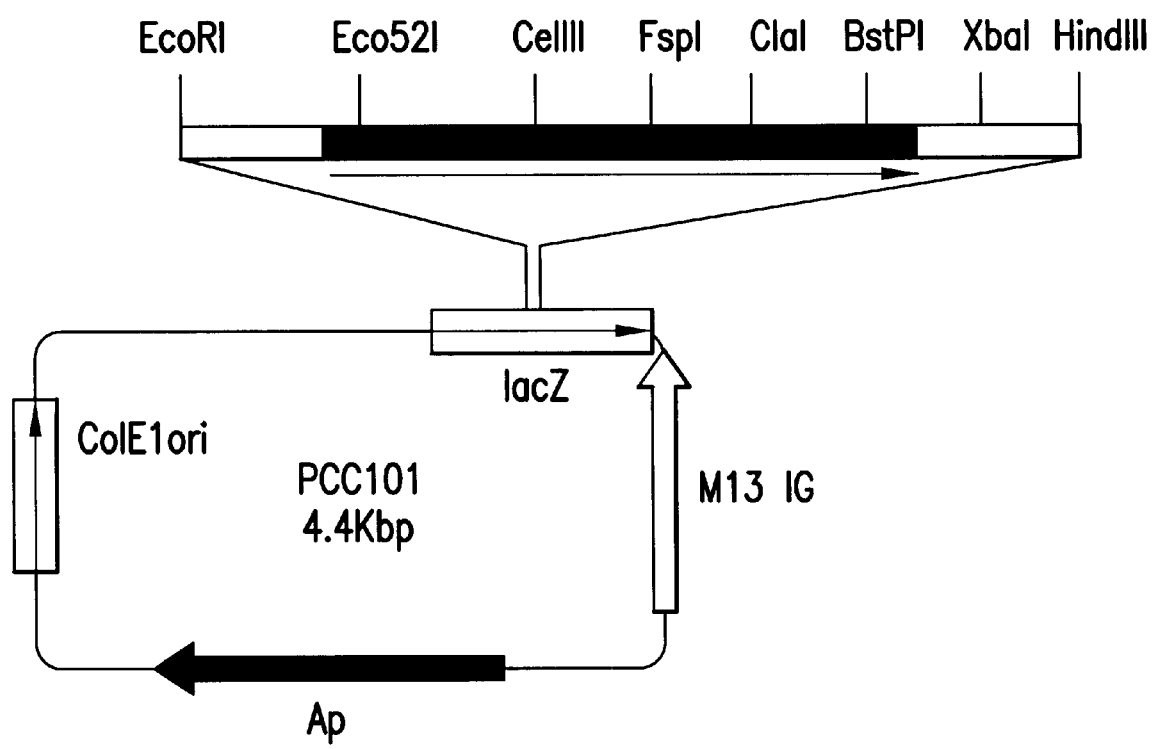
FIG. 3 is a view showing a restriction enzyme map of an expression plasmid pCC101 containing a gene encoding the wild-type esterase. In the figure, an open symbol indicates a DNA derived from Chromobacterium SC-YM-1 (FERM BP-6703) and a black part indicates the translation region of the wild-type esterase.

On one hand, the Sac I fragment (about 3.5 kbp) in pCC6 was subcloned into pUC118 (manufactured by Takara Shuzo Co., Ltd.) to make pCC30. This pCC30 was digested with Eco52I and SacI to excise a DNA fragment (about 1.2 Kbp) encoding the translation region of an esterase gene. On the other hand, pUC118 having the lac promoter was digested with EcoRI and SacI and treated with alkaline phosphatase. The Eco52I-SacI fragment containing the above DNA fragment (SD) and the translation region of the present gene was ligated to the region between the EcoRI site and the SacI site of this pUC118 using a DNA ligation kit (manufactured by Takara Shuzo Co., Ltd.) (FIG. 2) to make pCC101 (FIG. 3).

Example 5

Preparation of the Present Gene

1. Preparation of Mutant Primer

As a mutant primer for introducing an amino acid substitution Asn43Ser (amino acid substitution of Asn of 43rd amino acid with Ser), Thr240Ala (amino acid substitution of Thr of 240th amino acid with Ala), Val288Ala (amino acid substitution of Val of 288th amino acid with Ala), Val325Ile (amino acid substitution of Val of 325th amino acid with Ile) or Ala363Term (termination codon) (substitution of Ala of 363rd amino acid with the base sequence showing termination codon), synthetic oligonucleotides (mutant primers N43S, T240A, V288A, V325I, A363Term, RV-G, RV-C, RV-D, MY-2, MY-3, MY-6) were prepared having the base sequence corresponding to each amino acid as shown by FIG. 4 and SEQ ID Nos:12–22. These mutant primers were synthesized using a DNA synthesizer Model 394 manufactured by Applied Biosystems and purified with an oligonucleotide purifying cartridge manufactured by the same company.

2. Introduction of Site-directed Mutation

A mutant esterase was prepared according to a method of Olfert Landt, et al. (Gene, 96, 125–128, 1990).

2-1) Preparation of pCCN43S (example of substitution regarding 43rd amino acid)

DNA fragment was amplified with GeneAmpTM PCR Reagent kit (manufactured by Takara Shuzo Co., Ltd.) (1stPCR) using the mutant primer RV-G (100 pmol) shown by SEQ ID No:17 and the mutant primer N43S (100 pmol) shown by SEQ ID No:12 and using 500 ng of pCC101 obtained in Example 4 as a template DNA. The resultant PCR product (190 bp fragment) was purified using SUPREC-02 (manufactured by Takara Shuzo Co., Ltd.) column.

Subsequently, similarly, DNA fragment was amplified with GeneAmpTM PCR Reagent kit using the mutant primer MY-3 (50 pmol) shown by SEQ ID No:21 and the 190 bp DNA fragment (50 pmol) previously purified as a primer and using 500 ng of pCC101 as a template DNA. The amplified DNA fragment was digested with restriction enzymes NdeI and Bpu 1102 I , the sample was electrophoresed with 4% agarose gel (NuSieve3:1Agarose, manufactured by Takara Shuzo., Co., Ltd.), about 370 bp DNA fragments were separated and purified using GeneClean DNA purification kit (manufactured by Bio101).

Figure 5:
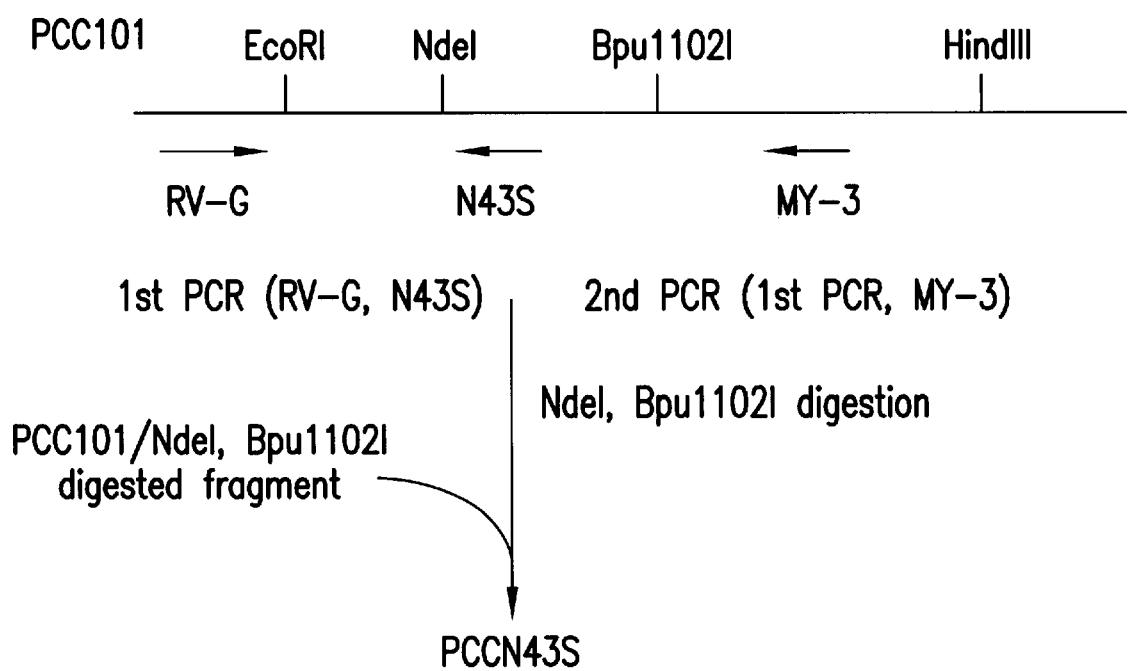
FIG. 5 is a view showing a step for constructing the plasmid pCCN43S containing the present gene.

On the other hand, 3 μg of pCC101 was digested with NdeI and Bpu1102I, and treated with alkaline phosphatase. Then, the NdeI-Bpu1102I fragment (4.2 Kbp) of this pCC101 and the previously prepared and obtained NdeI-Bpu1102I fragment (240 bp) in which mutation had been introduced were ligated using a DNA ligation kit (manufactured by Takara Shuzo Co., Ltd.), and transformed into *E. coli* strain JM109 according to the conventional method to make pCCN43S (FIG. 5).

2-2) Preparation of pCCT240A (Example of Substitution Regarding 240th Amino Acid)

DNA fragment was amplified with GeneAmpTM PCR Reagent kit (manufactured by Takara Shuzo Co., Ltd.) (1stPCR) using the mutant primer MY-6 (100 pmol) shown by SEQ ID No:22 and the mutant primer T240A (100 pmol) shown by SEQ ID No: 13 and using 500 ng of pCC101 obtained in Example 4 as a template DNA. The resultant PCR product (280 bp fragment) was purified using SUPREC-02 (manufactured by Takara Shuzo Co., Ltd.) column.

Subsequently, similarly, DNA fragment was amplified with GeneAmpTM PCR Reagent kit using the mutant primer RV-C (50 pmol) shown by SEQ ID No:18 and the 280 bp DNA fragment (50 pmol) previously purified as a primer and using 500 ng of pCC101 as a template DNA. The amplified DNA fragment was digested with restriction enzymes Bpu1102I and BstPI, the sample was electrophoresed with 4% agarose gel (NuSieve3:1Agarose, manufactured by Takara Shuzo Co., Ltd.), about 590 bp DNA fragments were separated and purified using GeneClean DNA purification kit (manufactured by Bio101 ).

Figure 6:
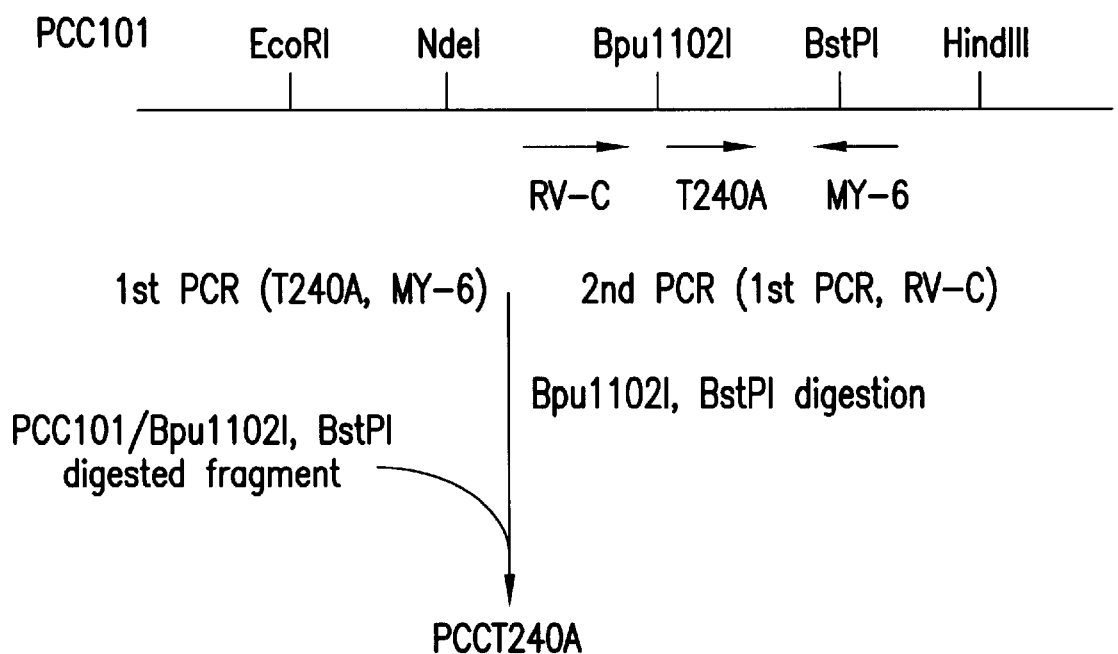
FIG. 6 is a view showing a step for constructing the plasmid pCCT240A containing the present gene.

On the other hand, 3 μg of pCC101 was digested with Bpu1102I and BstPI, and treated with alkaline phosphatase. Then, the Bpu1102I-BstPI fragment (3.8 Kbp) of this pCC101 and the previously prepared and obtained Bpu1102I-BstPI fragment (590 bp) in which mutation had been introduced were ligated using a DNA ligation kit (manufactured by Takara Shuzo Co., Ltd.), and transformed into *E. coli* strain JM109 according to the conventional method to make pCCT240A (FIG. 6).

2-3) Preparation of pCCV288A (Example of Substitution Regarding 288th Amino Acid)

DNA fragment was amplified with GeneAmp TMPCR Reagent kit (manufactured by Takara Shuzo Co., Ltd.) (1stPCR) using the mutant primer MY-6 (100 pmol) shown by SEQ ID No:22 and the mutant primer V288A (100 pmol) shown by SEQ ID No:14 and using 500 ng of pCC101 obtained in Example 4 as a template DNA. The resultant PCR product (130 bp fragment) was purified using SUPREC-02 (manufactured by Takara Shuzo Co., Ltd.) column.

Subsequently, similarly, DNA fragment was amplified with GeneAmpTM PCR Reagent kit using the mutant primer RV-C (50 pmol) shown by SEQ ID No:18 and the 130 bp DNA fragment (50 pmol) previously purified as a primer and using 500 ng of pCC101 as a template DNA. The amplified DNA fragment was digested with restriction enzymes Bpu1102I and BstPI, the sample was electrophoresed with 4% agarose gel (NuSieve3:1Agarose, manufactured by Takara Shuzo Co., Ltd.), about 590 bp DNA fragments were separated and purified using GeneClean DNA purification kit manufactured by Bio101.

Figure 7:
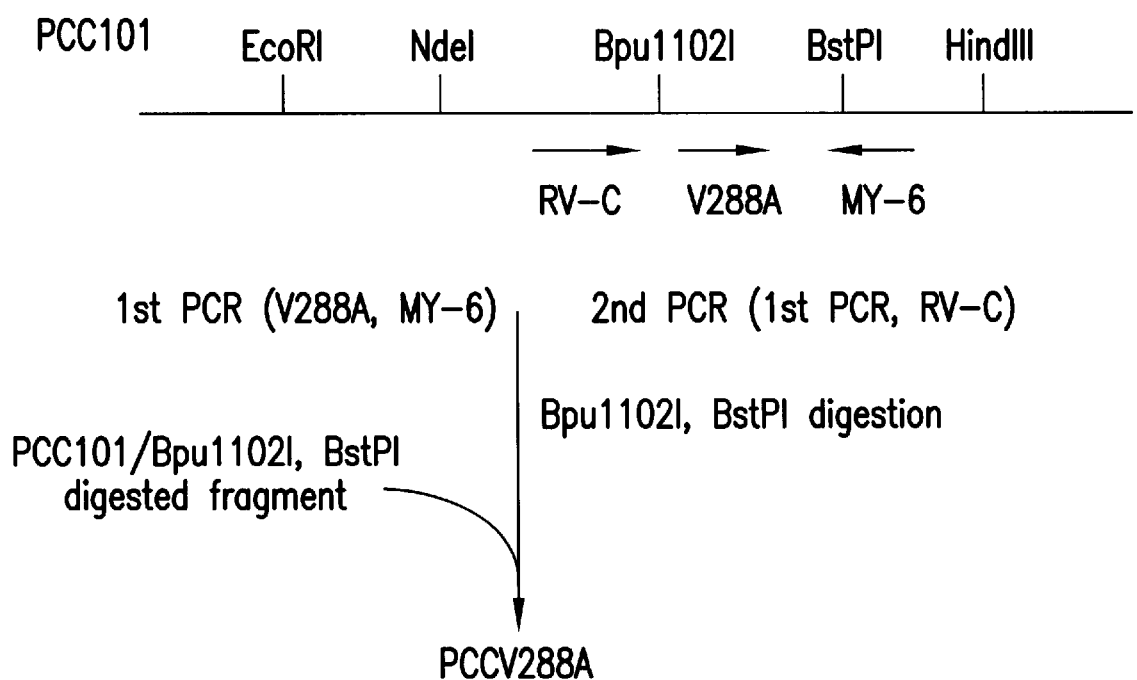
FIG. 7 is a view showing a step for constructing the plasmid pCCV288A containing the present gene.

On the other hand, 3 μg of pCC101 was digested with Bpu1102I and BstPI and treated with an alkaline phosphatase. Then, the Bpu1102I-BstPI fragment (3.8 Kbp) of this pCC101 and the previously prepared and obtained Bpu1102I-BstPI fragment (590 bp) in which mutation had been introduced were ligated using a DNA ligation kit (manufactured by Takara Shuzo Co., Ltd.), and transformed into *E. coli* strain JM109 according to the conventional method to make pCCV288A (FIG. 7).

2-4) Preparation of pCCV325I (Example of Substitution Regarding 325th Amino Acid)

DNA fragment was amplified with GeneAmpTM PCR Reagent kit (manufactured by Takara Shuzo Co., Ltd.) (1stPCR) using the mutant primer MY-2 (100 pmol) shown by SEQ ID No:20 and the mutant primer V325I (100 pmol) shown by SEQ ID No:15 and using 500 ng of pCC101 obtained in Example 4 as a template DNA. The amplified DNA fragment was digested with restriction enzymes BstPI and XbaI, the sample was electrophoresed with 4% agarose gel (NuSieve3:1Agarose, manufactured by Takara Shuzo Co., Ltd.), about 220 bp DNA fragments were separated and purified using GeneClean DNA purification kit manufactured by Bio101.

Figure 8:
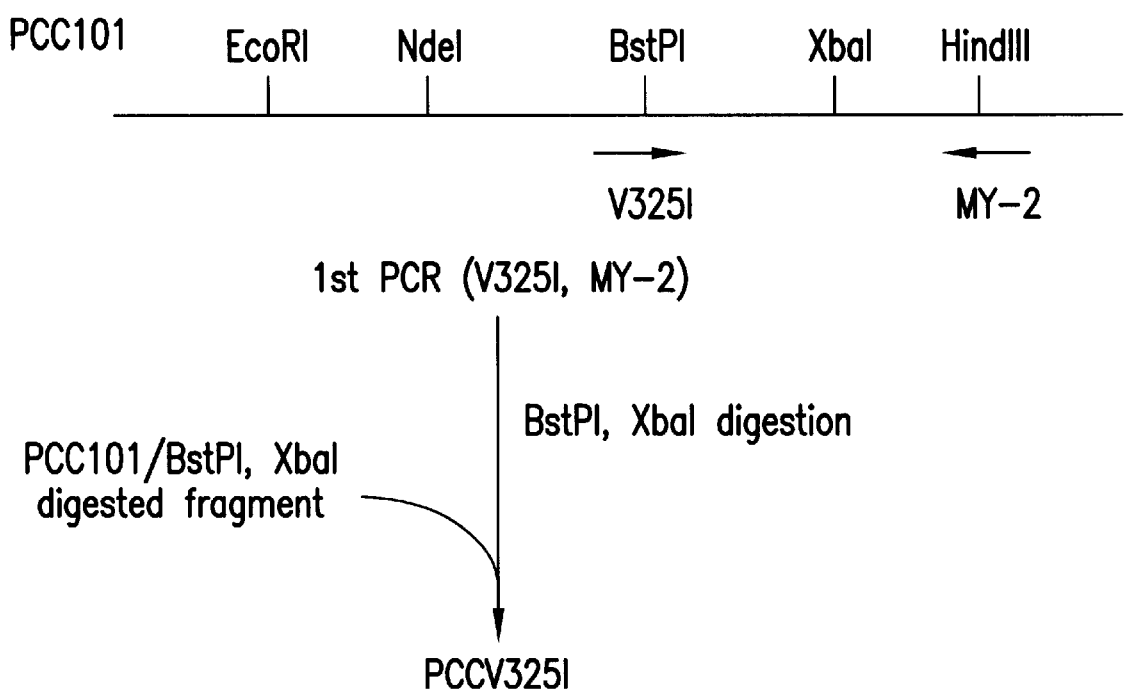
FIG. 8 is a view showing a step for constructing the plasmid pCCV325I containing the present gene.

On the other hand, 3 μg of pCC101 was digested with BstPI and XbaI and treated with alkaline phosphatase. Then, the BstPI-XbaI fragment (4.2 Kbp) of this pCC101 and the previously prepared and obtained BstPI-XbaI fragment (220 bp) in which mutation, had been introduced were ligated using a DNA ligation kit (manufactured by Takara Shuzo Co., Ltd.), and transformed into *E. coli* strain JM109 according to the conventional method to make pCCV325I (FIG. 8).

2-5) Preparation of pCCA363Term (Example of Substitution Regarding 363rd Amino Acid)

DNA fragment was amplified with GeneAmpTM PCR Reagent kit (manufactured by Takara Shuzo Co., Ltd.) (1stPCR) using the mutant primer MY-2 (100 pmol) shown by SEQ ID No:20 and the mutant primer A363term (100 pmol) shown by SEQ ID No:16 and using 500 ng of pCC101 obtained in Example 4 as a template DNA. The resultant PCR product (150 bp fragment) was purified using SUPREC-02 (manufactured by Takara Shuzo Co., Ltd.) column.

Subsequently, DNA fragment was amplified with GeneAmpTM PCR Reagent kit using the mutant primer RV-D (50 pmol) shown by SEQ ID No:19 and the 150 bp DNA fragment (50 pmol) previously purified as a primer and using 500 ng of pCC101 as a template DNA. The amplified DNA fragment was digested with restriction enzymes BstPI and XbaI, the sample was electrophoresed with 4% agarose gel (NuSieve3:1Agarose, manufactured by Takara Shuzo Co., Ltd.), about 220 bp DNA fragments were separated and purified using GeneClean DNA purification kit manufactured by Bio101.

Figure 9:
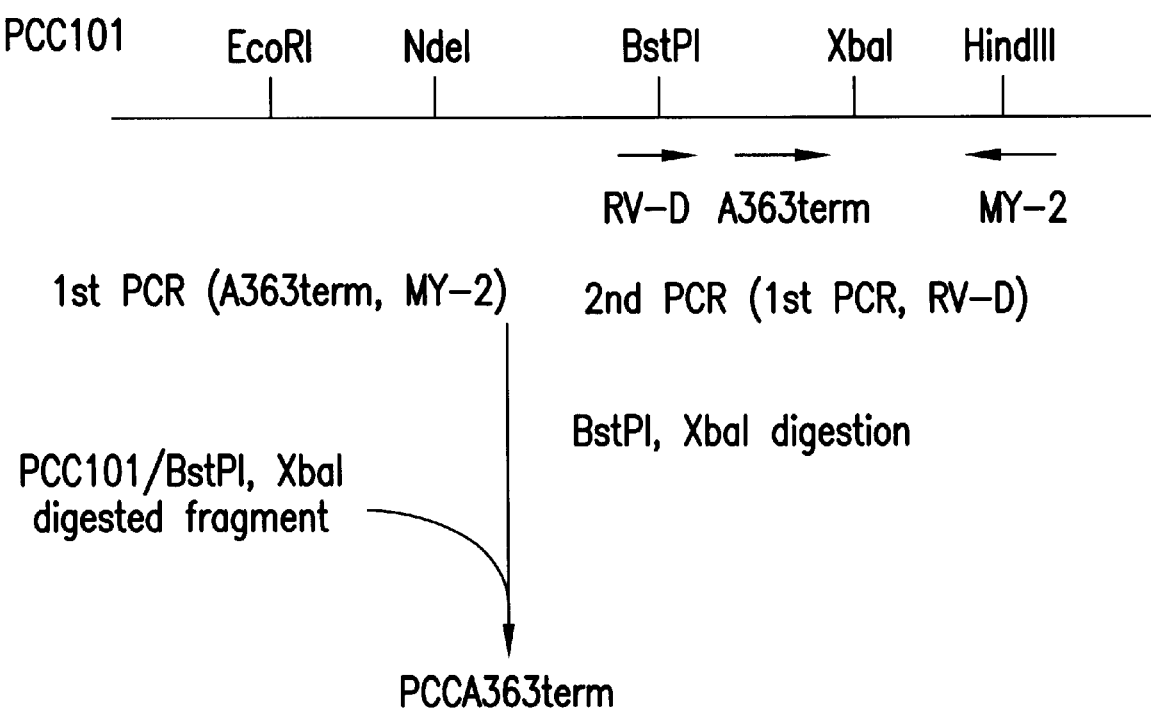
FIG. 9 is a view showing a step for constructing the plasmid pCCA363term containing the present gene.

On the other hand, 3 μg of pCC101 was digested with BstPI and XbaI and treated with alkaline phosphatase. Then, the BstPI-XbaI fragment (4.2 Kbp) of this pCC101 and the previously prepared and obtained BstPI-XbaI fragment (220 bp) in which mutation had been introduced were ligated using a DNA ligation kit (manufactured by Takara Shuzo Co., Ltd.), and transformed into E. coli strain JM109 according to the conventional method to make pCCA363term (FIG. 9).

3. Introduction of Multiple Mutation 3-1) Preparation of pCCN43SA363Term (Example of Substitution Regarding 43rd and 363rd Amino Acids)

Figure 10:
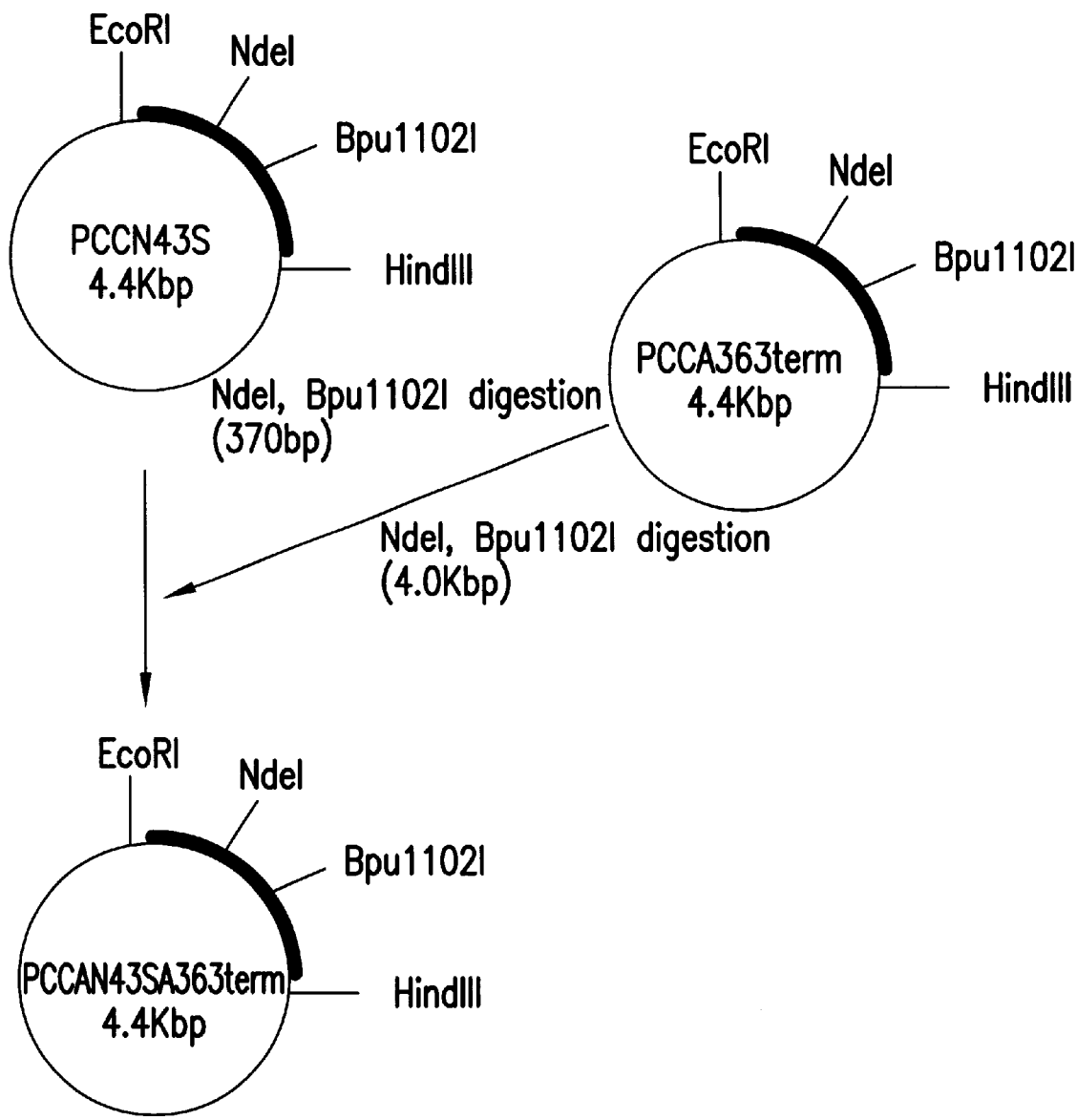
FIG. 10 is a view showing a step for constructing the plasmid pCCN43SA363term containing the present gene.

10 μg of pCCN43S obtained in 2-1) was digested with NdeI and Bpu1102I to obtain 370 bp fragment. On the other hand, 3 μg of pCCA363term was digested with NdeI and Bpu1102I and treated with alkaline phosphatase. Then, NdeI-Bpu1102I fragment (4.2 Kbp) of this pCCA363term and the previously prepared and obtained NdeI-Bpu1102I fragment (370 bp) were ligated using DNA ligation kit (manufactured by Takara Shuzo Co., Ltd.) and transformed into E. coli strain JM109a according to the conventional method to obtain the plasmid pCCN43SA363term containing the present multiple mutation gene (FIG. 10).

3-2) Preparation of pCCT240AV288A (Example of Substitution Regarding 240th and 288th Amino Acids)

Figure 11:
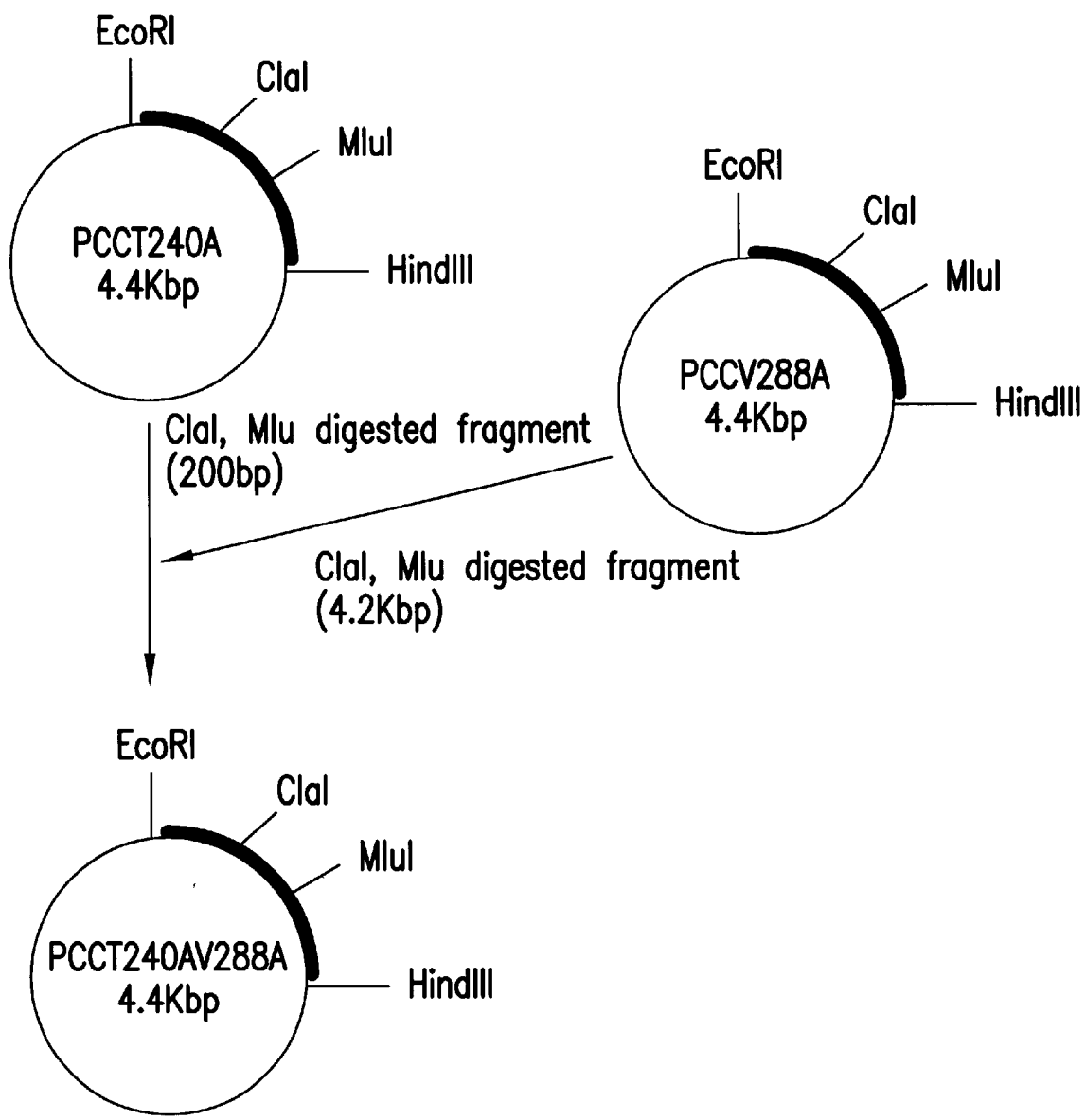
FIG. 11 is a view showing a step for constructing the plasmid pCCT240V288A containing the present gene.

10 μg of pCCT240A obtained in 2—2) was digested with ClaI and MluI to obtain 200 bp fragment. On the other hand, 3 μg of pCCV288A was digested with ClaI and MluI and treated with alkaline phosphatase. Then, ClaI-MluI fragment (4.4 Kbp) of this pCCV288A and the previously prepared and obtained ClaI-MluI fragment (200 bp) were ligated using DNA ligation kit (manufactured by Takara Shuzo Co., Ltd.) and transformed into E. coli strain JM109 according to the conventional method to obtain the plasmid pCCT240AV288A containing the present multiple mutation gene (FIG. 11).

Example 6

Production of the Present Esterase by Transformant Microorganism

Total four strains of recombinant E. coli in which 3 kinds of the present esterase expression plasmids were introduced (JM109/pCCN43SA363term, JM109/pCCT240AV288A, JM109/pCCV325I) obtained in Example 5 and the transformant E. coli in which the wild-type esterase expression vector was introduced (JM109/pCC101) were inoculated on 50 mL (500 mL flask) of an LB medium (tryptone 1 (w/v) %, yeast extract 0.5 (w/v) %, NaCl 0.5 (w/v) %), cultured by shaking at 37° C. and IPTG (isopropyl-β-D-thiogalactopyranoside) was added to the final concentration of 1 mM at logarithmic growth phase (about 2 hours after initiation of culturing), followed by further culturing for 4 hours.

The cells were collected by centrifugation (8000×g, 10 minutes, 4° C.), and a sample prepared from the cells (having an equivalent amount to an amount of cells contained in 5 μl of culturing medium) was analyzed by SDS-PAGE, as a result protein was recognized as a main band at the position corresponding to the molecular weight of the present esterase in all the four samples.

Example 7

Purification of the Present Esterase

Four kinds of transformant E. coli which had been cultured according to the manner as in Example 6 were ultrasonically disrupted (20 KHz, 15 minutes, 4° C.), respectively, and centrifuged (12000×g, 30 minutes, 4° C.) to obtain the supernatant. 150 ml of the resulting supernatant was passed through a column filled with 200 ml of a negative ion-exchange resin (DEAE-Sepharose fastflow, manufactured by Pharmacia). The column was washed with 0.15M NaCl+10 mM Tris-HCl buffer (pH 7.5) and the present esterase was eluted with 0.15–0.35M NaCl linear concentration gradient. Measurement of the activities of the eluted fractions was performed using p-nitrophenyl acetate (pNPA) which is a general substrate for esterase. More particularly, 5 mM of a substrate dissolved in acetonitrile was added to 1.0 ml of 10 mM phosphate buffer (pH 7.5) containing the eluted fraction, which was maintained at 37° C. and an increase in absorbance at 410 nm was measured. The fractions in which the esterase activity was shown were collected, and the fractions were passed through a column filled with 200 ml of a hydrophobic resin (Butyl-Toyopearl 650S, manufactured by Toyosodakogyo). The column was washed with 10% (w/v) $(NH_4)_2SO_4$+10 mM Tris-HCl buffer (pH 7.5), and the present esterase was eluted with 10-0% (w/v) saturated ammonium sulfate linear concentration gradient. The fractions in which the esterase activity was shown were collected and adopted as a purified enzyme (hereinafter referred to as the present esterase N43SA362term, T240AV288A and V325I, and the wild-type (WT)).

Example 8

Measurement of the Thermostability of the Present Esterase

The thermal stability of four kinds of purified enzymes obtained in Example 3 was measured according to the following procedures.

1.0 ml of 10 mM phosphate buffer (pH 7.5) with 10 μg/ml of the above purified enzyme added was maintained at 70° C. for 120 minutes and the activity of the present esterase was measured. Measurement of the activity was performed using p-nitrophenyl acetate (pNPA) which is a general substrate for esterase. More particularly, 5 mM substrate dissolved in acetonitrile was added to the test solution after maintaining a temperature, maintained at 37° C. and absorbance at 410 nm was measured. The results are shown in Table 1. A rate of the activity after temperature maintenance at 70° C. for 120 minutes to that before the temperature maintenance is expressed as remaining activity percentage and a rate of the remaining activity of the present-esterase when the remaining activity percentage of the wild-type esterase (WT) is regarded as 100 is shown as the remaining activity ratio (to that of WT).

TABLE 1

| | Remaining activity ratio (to that of WT) | Remaining activity percentage (%) | Remarks |
|---|---|---|---|
| N43SA363term | 173 | 60.0 | Amino acid substitution in which 43rd amino acid in the amino acid sequence shown by SEQ ID: NO. 2 is substituted with serine |
| T240AV288A | 171 | 59.3 | Amino acid substitution in which 240th amino acid in the amino acid sequence shown by SEQ ID: NO. 2 is substituted with alanine and 288th amino acid is substituted with alanine |
| V325I | 163 | 56.6 | Amino acid substitution in which 325th amino acid in the amino acid sequence shown by SEQ ID: NO. 2 is substituted with isoleucine |
| Wild-type esterase (WT) | 100 | 34.7 | |

As mentioned above, the present invention makes possible to provide an esterase which may be utilized for organic synthesis reaction for manufacturing medicaments, pesticides or intermediates thereof and is excellent in thermostability.

---

What is claimed is:

1. An isolated nucleotide sequence encoding a modified esterase having thermostable esterase activity, which is obtained by modifying the amino acid sequence shown by SEQ ID NO:2 and where the modification is selected from any one of the following:

(1) an amino acid substitution where the 325th amino acid in the amino acid sequence shown by SEQ ID No:2 is substituted with isoleucine;

(2) an amino acid substitution where the 240th amino acid in the amino acid sequence shown by SEQ ID No:2 is substituted with alanine, and 288th amino acid is substituted with alanine; and (3) an amino acid substitution where 43rd amino acid sequence shown by SEQ ID No:2 is substituted with serine.

2. A plasmid which is characterized in that it contains the nucleotide sequence of claim 1.

3. A microorganism which is characterized in that it contains the plasmid of claim 2.

4. A process for producing an esterase comprising the steps of:

culturing the microorganism of claim 3 under conditions in which the microorganism produces a modified esterase having thermostable esterase activity and the amino acid sequence shown by SEQ ID NO:2, wherein the modification is selected from any one of the following:

(1) an amino acid substitution where the 325 th amino acid in the amino acid sequence shown by SEQ ID NO:2 is substituted with isoleucine;

(2) an amino acid substitution where the 240 th amino acid in the amino acid sequence shown by SEQ ID NO:2 is substituted with alanine and 288 th amino acid is substituted with alanine; and (3) an amino acid substitution where the 43 rd amino acid in the amino acid sequence shown by SEQ ID NO:2 is substituted with serine.

* * * * *